United States Patent [19]

Chen et al.

[11] Patent Number: 4,623,721

[45] Date of Patent: Nov. 18, 1986

[54] SYNTHESIS OF L-FRUCTOSE AND DERIVATIVES THEREOF

[75] Inventors: Chyi-Cheng Chen, Gaithersburg, Md.; Roy L. Whistler, West Lafayette, Ind.

[73] Assignee: Purdue Research Foundation, West Lafayette, Ind.

[21] Appl. No.: 613,184

[22] Filed: May 23, 1984

[51] Int. Cl.$^4$ .......................... C07H 1/00; C07H 9/04; C07H 3/10

[52] U.S. Cl. .................................. 536/4.1; 536/18.5; 536/55; 536/18.1; 536/124; 536/125

[58] Field of Search ...................... 536/4.1, 18.1, 18.5, 536/55, 124, 125

[56] References Cited

U.S. PATENT DOCUMENTS

| | | | |
|---|---|---|---|
| 3,451,993 | 6/1969 | Goshima et al. | 536/18.5 |
| 3,505,309 | 4/1970 | Carubelli | 536/125 |
| 3,514,327 | 5/1970 | Parrish | 536/125 |
| 4,350,811 | 9/1982 | Holland et al. | 536/55 |
| 4,429,117 | 1/1984 | Koebernick et al. | 536/55 |

OTHER PUBLICATIONS

Wolfrom, "Advances in Carbohydrate Chemistry", vol. 13, 1958, Academic Press Inc., New York, N.Y., pp. 63–69.
Guthrie et al., "Chem. Abst.", vol. 94, 1981, p. 47695(m).
Guthrie et al., "Chem. Abst.", vol. 95, 1981, p. 133304(k).
Guthrie et al., "Chem. Abst.", vol. 97, 1982, p. 6682(y).

Primary Examiner—Johnnie R. Brown
Attorney, Agent, or Firm—Roylance, Abrams, Berdo & Goodman

[57] ABSTRACT

It is disclosed that L-fructose can be produced in high yield from L-sorbose. The process involves the inversion of the hydroxyl groups on carbon atoms C3 and C4 of L-sorbose to produce L-fructose. This inversion can be accomplished in simple, commercial equipment with the aid of common reagents. L-sorbose or an appropriately blocked derivative thereof is reacted so as to introduce or create a good leaving group, preferably mesyl or tosyl, at chiral carbon C3 thereby displacing the hydroxyl previously at that position. The leaving group is then displaced, preferably under alkaline conditions, in such a way that the hydroxyl oxygen atom at chiral carbon C4 attaches to chiral carbon C3, thereby displacing the leaving group while forming a 3,4-oxirane (epoxide) ring. The 3,4-oxirane ring forms in a downward position relative to the Haworth presentation thereby inverting chiral carbon C3 during formation of the 3,4-oxirane ring.

The 3,4-oxirane ring is then opened under acidic or alkaline conditions to yield a sugar ring with a hydroxyl group in a position above the sugar ring at chiral carbon C4, and a hydroxyl group in a downward position at C3.

Removal of any remaining blocking groups yields L-fructose. This may be accomplished by acid hydrolysis.

There are also disclosed novel classes of compounds which act as intermediaries in the synthesis of L-fructose.

14 Claims, No Drawings

SYNTHESIS OF L-FRUCTOSE AND DERIVATIVES THEREOF

BACKGROUND OF THE INVENTION

There is a great need in the food industry for a sweet, zero calorie, non-toxic sugar. An ideal example would be a nonmetabolizable fructose. D-Fructose, the sweetest natural sugar, provides excellent organoleptic acceptance and mouth feel. The United States uses over 23 billion pounds of sucrose per year and some of it is hydrolyzed to its constituent sugars namely one unit of D-glucose and one unit of D-fructose. The mixture is commercially called invert sugar. Since D-fructose is 1.7 times as sweet as sucrose, and D-glucose 0.7 times as sweet as sucrose, the total sweetness of invert sugar is higher than that of sucrose. With the advent of enzyme engineering, it has become possible to convert D-glucose to an equilibrium mixture of D-glucose and D-fructose in a proportion of 54% to 46% respectively, and hence, produce the sweetness of invert sugar from low cost D-glucose, a product of the corn wet milling industry. As a consequence, the use of fructose in the food industry has increased extensively.

With all of the desirable advances in producing the sweet sugar D-fructose, there has been no reduction in caloric value except for the lesser amount of D-fructose required to give the same sweetness as sucrose. Both D-glucose and D-fructose are completely and equally metabolized in humans to produce equivalent caloric energy.

With the health need to take in less calories, some of the normal metabolic sugars should be replaced with other acceptable nonmetabolizable and non-toxic sweeteners. This has been done with the development of synthetic sweeteners such as saccharin and aspartame. However, a much more desirable sweetener is L-fructose which has the same sweetness as natural D-fructose. It has no toxicity and seems not to be metabolized by humans, thus yielding no caloric value. L-Fructose is the mirror image of D-fructose. It has the same taste and most of the other properties of D-fructose but is not a substrate for the metabolic enzymes of the human system.

Examples of sweetened substrates which may be prepared with L-fructose can be found in U.S. Pat. No. 4,262,032 to Levin which is expressly incorporated herein. This patent describes and claims the use of L-fructose and other L-hexose monosaccharides as sweetening agents.

L-Fructose, which has not been found in nature, was synthesized for the first time by Fischer. See E. Fischer, Ber., 23 (1890) 370-394. DL-Glucose phenylosazone was prepared from α-acrose and hydrolyzed to the glycosulose, which was reduced to DL-fructose. L-Fructose was isolated from the mixture. L-Fructose was later synthesized by Wolfrom and Thompson from L-arabinonic acid in five steps. See M. L. Wolfrom and A. Thompson, Methods of Carbohydr. Chem., 1 (1962) 118-120.

Recently, L-fructose was prepared by aldol condensation. See S. Morgenlie, Carbohydr. Res., 107 (1982) 137-141. DL-Glyceraldehyde condensed with 1,3-dihydroxy-2-propanone catalyzed by Dowex 1 (OH$^-$) resin to give a hexulose mixture. Crystallization of the mixture from methanol yielded 54% of DL-fructose. Treatment of the DL-fructose mixture with baker's yeast gave a product from which 62% of 2,3:4,5-di-O-isopropylidene-$\beta$-L-fructopyranose was isolated after acetonation. When L-glyceraldehyde was used as starting material, 2,3:4,5-di-O-isopropylidene-$\beta$-L-fructopyranose was isolated in 60-65% yield after acetonation of the hexulose mixture.

L-Fructose has been prepared enzymatically from L-mannose by an isomerase present in cell-free extracts of Aerobacter aerogenes grown on L-mannose to give L-fructose in 28-32% yield. See J. W. Mayo and R. J. Anderson, Carbohydr. Res., 8 (1968) 344-347.

Both chemical and enzymic procedures either are too elaborate or require relatively expensive starting material. To commercialize L-fructose as a sweetener requires a low cost process. A simple method for the synthesis of L-fructose which starts with L-sorbose, a relatively inexpensive industrial chemical would be desirable. The only structural difference between L-sorbose and L-fructose is the reverse configuration of the hydroxyl groups at C-3 and C-4.

SUMMARY OF THE INVENTION

It has now been discovered that L-fructose can be produced in high yield from L-sorbose. The process is simple and convenient to conduct. The process involves the inversion of the hydroxyl groups on carbon atoms C3 and C4 of L-sorbose to produce L-fructose. This inversion can be accomplished in simple, commercial equipment with the aid of common reagents.

In accordance with the present invention, L-sorbose or an appropriately blocked derivative thereof is reacted so as to introduce a good leaving group, preferably mesyl or tosyl, at chiral carbon C3 thereby replacing the proton of the hydroxyl previously at that position. The leaving group is then displaced, preferably under alkaline conditions, in such a way that the hydroxyl oxygen atom at chiral carbon C4 attaches to chiral carbon C3, thereby displacing the leaving group while forming a 3,4-oxirane (epoxide) ring. The 3,4-oxirane ring forms in a downward position relative to the Haworth representation in which the ring oxygen atom is to the right and behind the plane of the paper thereby inverting chiral carbon C3 during formation of the 3,4-oxirane ring.

The 3,4-oxirane ring is then opened under acidic or alkaline conditions to yield a sugar ring with a hydroxyl group in a position above the sugar ring at chiral carbon C4, and a hydroxyl group in a downward position at C3.

Removal of any remaining blocking groups yields L-fructose. This may be accomplished, for example, by acid hydrolysis.

Also, in accordance with the above-described process, two novel classes of compounds are disclosed which act as intermediaries in the synthesis of L-fructose. These are a 3,4-anhydro-L-sorbose having the formula:

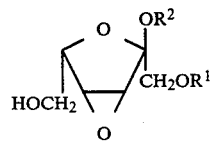

wherein $R^1$ represents a good leaving group, $R^2$ represents a (lower)alkyl group, or $R^1$ and $R^2$ both are attached to a good leaving group and an L-sorbofuranose derivative selected from those having the formulas

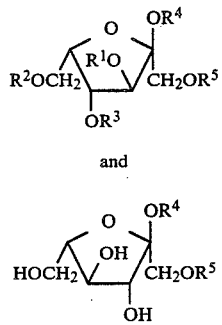

and wherein $R^1$ represents a good leaving group, $R^2$ and $R^3$ represent hydrogen or together are attached to a good leaving group, $R^4$ represents a (lower)alkyl group, $R^5$ represents a good leaving group, or $R^4$ and $R^5$ taken together represent a (lower)divalent hydrocarbon group.

DETAILED DESCRIPTION OF THE INVENTION

There are several modifications of L-sorbose that can serve as starting materials for the conversion. Each is easily made and serves well in the conversion process. Each can be made by any of several well known processes.

Among such convenient starting materials are methyl L-sorbofuranoside, 1,2-O-isopropylidene-L-sorbofuranose, 1,2-O-isopropylidene-L-sorbopyranose, 2,3-O-isopropylidene-L-sorbofuranose, 2,3-O-isopropylidene-L-sorbopyranose, 1,3-O-isopropylidene-L-sorbofuranose, 1,3-O-isopropylidene-L-sorbopyranose, 1,2:4,6-di-O-isopropylidene-L-sorbofuranose, 2,3:4,6-di-O-isopropylidene-L-sorbofuranose, 1,3:4,6-di-O-isopropylidene-L-sorbofuranose, methyl 4,6-O-isopropylidene-L-sorbofuranoside, ethyl 4,6-O-isopropylidene-L-sorbofuranoside, methyl 1,3:4,6-di-O-isopropylidene-L-sorbofuranoside, and ethyl 1,3:4,6-di-O-isopropylidene-L-sorbofuranoside. Other appropriately blocked starting materials, such as appropriately blocked L-sorbofuranosides, will be apparent to those knowledgeable in carbohydrate chemistry.

The isopropylidene blocking group can be prepared in many ways using a variety of reagents, such as acetone and 2,2-dimethoxypropane. The isopropylidene blocking group can be replaced by other blocking groups, such as benzylidene, ethylidene, sec. butylidene and cyclohexylidene.

Each of the starting materials can be derivatized at position C3 with a good leaving group such a tosyl, mesyl or other, such that on treatment under alkaline condition, as for example with sodium hydroxide or sodium methoxide, the leaving group can be displaced by the oxygen atom of the hydroxyl group at C4 to produce a three membered 3,4-oxirane ring wherein the 3,4-oxirane ring is below the sugar ring as it is in Haworth representation with the epoxide oxygen bonds being on the right side of the sugar if it were written upright in a normal Fischer projection. The formation of this particularly designed 3,4-oxirane ring rather than one of another steric arrangement is a prime discovery of this invention, for not only is the ring in correct position for the next conversion step, it is obtained in nearly 100% yield.

The next and last conversion step is to hydrolytically open the 3,4-oxirane ring with either acid or base to produce L-fructose or an L-fructose derivative which on acid treatment will yield L-fructose. Another discovery of merit, in the conversion, is the finding that the 3,4-oxirane ring opens specifically in the correct direction maintaining chiral configuration at carbon C3 while inverting chirality at carbon C4.

The process for converting L-sorbose to L-fructose is especially useful because it has been discovered that it is possible to treat an appropriate derivative of L-sorbose so as to introduce in high yield a good leaving group at chiral carbon C3 and to displace this group in such a way to give nearly 100% yield of a 3,4-oxirane ring involving chiral carbon C3 and C4 with concommitant inversion of chiral carbon atom C3.

The process is also most useful because of the finding that the 3,4-oxirane produced as described above can be opened in nearly 100% yield in such a manner that the chiral carbon atom at C4 is inverted by introduction of a hydroxyl group from the top side of the ring at C4 and hence, opposite to the oxygen bond at C4 involved in the 3,4-oxirane ring formation.

Various good leaving groups can be introduced at chiral carbon C3 of an L-sorbose derivative. P-Toluenesulfonyl (tosyl) and methylsulfonyl (mesyl) are preferred with mesyl especially preferred because of its low cost and ease of recovery and recycle.

The entire process of converting L-sorbose or an appropriately blocked L-sorbose derivative to L-fructose is amazingly low cost involving introducing the appropriate leaving group at chiral carbon C3, treating with alkali and then with acid. Both the alkali treatment and acid treatment can be conducted in the same reaction vessel without isolation or purification of the intermediate 3,4-oxirane derivative.

If good leaving groups are introduced at other positions than chiral carbon atom C3, no harm occurs since they will be hydrolyzed and removed in the last acid treatment step. It is preferred that a leaving group not be attached to carbon atom C4 or to another carbon where it can adversely effect the desired 3,4-oxirane ring formation at C3 and C4.

A preferred embodiment may be illustrated by the following reaction scheme:

PREFERRED EMBODIMENT 1

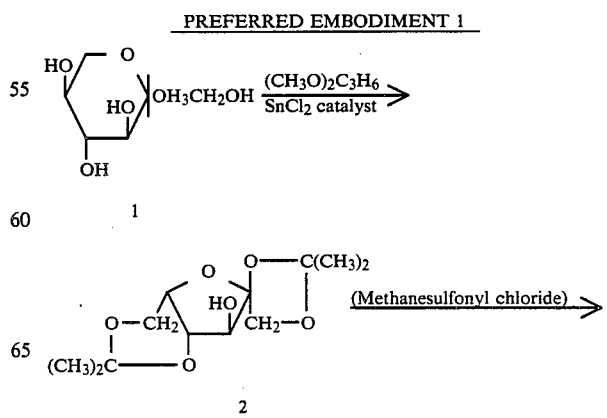

-continued
PREFERRED EMBODIMENT 1

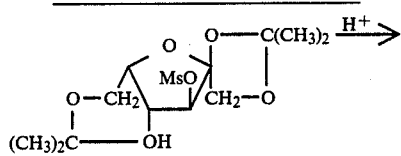

3

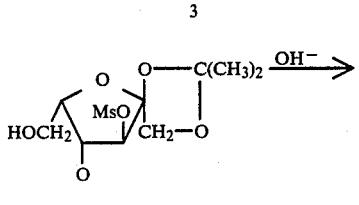

4

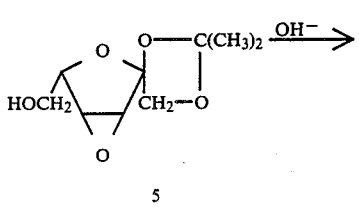

5

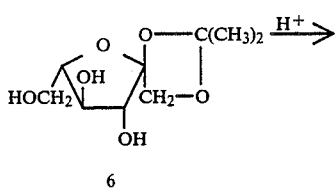

6

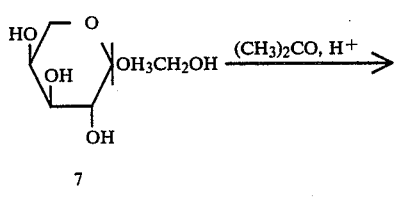

7

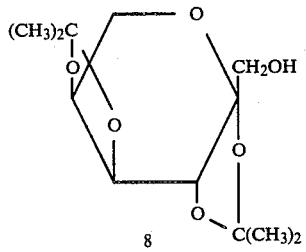

8

In this first preferred embodiment, L-fructose (7) is synthesized from L-sorbose (1) via a 1,2:4,6-di-O-isopropylidene-α-L-sorbofuranose (2) intermediate.

L-Sorbose can react with acetone or 2,2-dimethoxypropane to produce 2. 1,2:4,6-Di-O-isopropylidene-α-L-sorbofuranose (2), a kinetic product in the isopropylidenation of L-sorbose, is formed normally in about 5% yield. However, using tin(II) chloride as a catalyst, 2 can be obtained in greater than 80% yield as indicated by thin layer chromatography. The reaction is slow unless a small amount of 1,2-dimethoxyethane or acetone is present to improve the solubility of tin(II) chloride. 1,2-Dimethoxyethane is preferred for highest yield.

If acetone replaces 1,2-dimethoxyethane as a solvent, the yield may be somewhat lower. The yield can still be maintained high, however, by keeping the proportion of acetone in the reaction mixture as low as possible. A small amount of acetone is required as solvent for the reaction because tin(II) chloride is not soluble in 2,2-dimethoxypropane.

Compound 2 is then reacted with methanesulfonylchloride. Mesylation of 2 is complete in 1-4 hours to yield 1,2:4,6-di-O-isopropylidene-3-O-mesyl-α-L-sorbofuranose (3) in 83% yield. Compound 3 crystallizes readily from the reaction mixture upon the addition of water. Preferably, compound 3 is prepared from L-sorbose without isolation of the intermediate 2.

The 4,6-O-isopropylidene protecting group of 3 is selectively removed to yield 1,2-O-isopropylidene-3-O-mesyl-α-L-sorbofuranose (4) by addition of either a mixture of acetone and 0.25% aqueous sulfuric acid at 25° C. or 60% acetic acid at 40° C. The sulfuric acid reagent is better in terms of the cost and simplification of the process. A small amount of by-product, likely 3-O-mesyl-L-sorbose, is also detected, particularly in the 0.25% sulfuric acid medium. Compound 4 is crystalized from the reaction mixture after most of the acetone is removed.

Formation of the 3,4-anhydro ring is readily achieved in alkaline condition at 25° C. to yield 5. The alkali concentration and/or the proportion of methanol in the reaction mixture is critical. For example, when a solution of 4 in methanol (100 ml) and 1N sodium hydroxide (70 ml) is heated at 45° C. for 5 hours, only a very small amount of 4 is converted to 5.

Opening of the anhydro ring, however, is more difficult. Ring opening is completed in strong, aqueous alkaline solution by heating 3 days at 70°-80° C. A small amount of by-product is detected. On the other hand, a solution of 4 in 5% aqueous potassium hydroxide solution, refluxed for 3 hours, gives 6 as a single product.

Removal of the 1,2-O-isopropylidene group from 6 by acid hydrolysis gives 7 as the major product.

L-Fructose can be derivatized according to reported procedures to yield 8. See S. Morgenlie, Carbohydrate. Res., 107 (1982) 137-141. Compound 8 had the same m.p. and optical rotation as reported in the literature.

A second preferred embodiment for producing L-fructose from L-sorbose utilizes methyl 4,6-O-isopropylidene-1-3-di-O-tolylsulfonyl-α-L-sorbofuranoside (10) as an intermediate.

This second preferred embodiment may be illustrated by the following reaction scheme.

PREFERRED EMBODIMENT 2

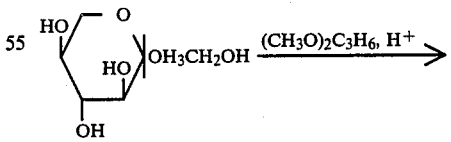

1

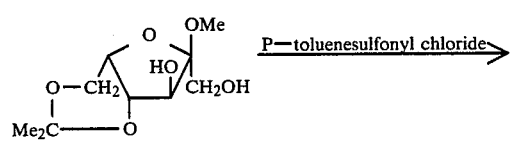

9

-continued
PREFERRED EMBODIMENT 2

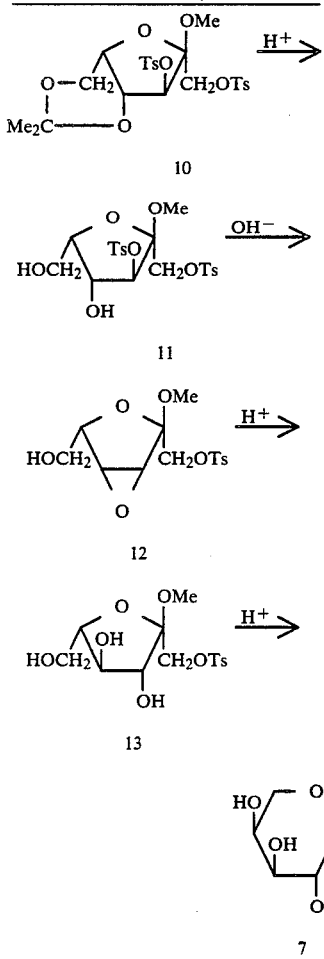

Methyl 4,6-O-isopropylidene-α-L-sorbofuranoside (9) is prepared in one step following reported procedures. See T. Maeda, K. Tori, S. Satoh and K. Tokuyama, Bull. Chem. Soc. Japan, 41 (1968) 2495–2503. Compound 9 is then reacted with a solution containing p-toluenesulfonyl chloride. Tosylation of 9 is complete in two days to give 10 and a trace amount of methyl 4,6-O-isopropylidene-1-O-p-tolysulfonyl-α-L-sorbo-furanoside.

The isopropylidene group of 10 is readily removed in 60% acetic acid solution to give 11. The reaction mixture is made alkaline to form a 3,4-anhydro-ring by intramolecular nucleophilic displacement of the sulfonyloxy group. The alkali concentration and/or the proportion of methanol in the reaction mixture is critical. For example, when a solution of 11 in methanol (100 ml) and 1N sodium hydroxide (70 ml) is heated at 45° C. for 5 hours, only a very small amount of 11 is converted to 12. The conditions required for alkaline scission of three membered anhydro-rings are, in general, more drastic than the conditions used for ring closure. No anhydro-ring opening is detected under the alkaline conditions used in this latter reaction.

Under milder, acidic conditions, 12 is converted to 13. The anhydro-ring is hydrolyzed but the glycosidic bond and the sulfonyl ester linkage survive. The p-toluenesulfonyl ester linkage is relatively resistant to acid hydrolysis with the glycosidic bond stabilized by the inductive effect from the adjacent sulfonyl ester group.

Because of the difficulty in cleaving the sulfonyl ester linkage, a high concentration of sulfuric acid (10N) is employed. The anhydro-ring opens exclusively at C4. This apparently favors the development of a positive charge at C4 rather than at C3 because of the inductive effect from the substituents at C1 and C2. The major product from the acid hydrolysis is L-fructose (7). Some minor products are also detected.

Crystalline 7 shows an optical rotation of about +60° within 30 minutes after dissolution. The optical rotation raises to +88° after 48 hours at 25° C. The increase in optical rotation indicates that the crystalline material is a β-L-anomer.

L-Fructose (7), when subjected to a tasting panel for sweetness is found to be as sweet as D-fructose.

The following Examples illustrate the procedures described in the first embodiment.

1,2:4,6-Di-O-isopropylidene-3-O-mesyl-α-L-sorbofuranose (3) was prepared as follows.

EXAMPLE 1

L-Sorbose (1, 8.24 g) was suspended in 1,2-dimethoxyethane (25 ml) containing tin(II) chloride (10 mg) and 2,2-dimethoxypropane (13.4 ml) was added. The mixture was refluxed, with stirring, for 2 hours until the solution was clear. A drop of pyridine was added and the mixture was concentrated to a syrup. The syrup was dissolved in chloroform and washed with water. The chloroform fraction was dried ($Na_4SO_4$) and evaporated to a syrup. The syrup was extracted with hot petroleum ether. Crystallization occurred from the cooled extract. Recrystallization from petroleum ether gave 2 (4.88 g, 41%), m.p. 71°–73°, $[\alpha]_D^{25} -24.7°$ (c 1.029, acetone); literature m.p. 72°–73° 8 $\alpha]_D^{25} -23.9$. The mass spectrum showed the largest fragment ion at m/e 245 ($M^+ - CH_3$).

Anal. Calc. for $C_{12}H_{20}O_6$; C, 55.37; H, 7.75. Found: C, 54.93; H, 7.67.

To a solution of 2 (0.7 g) in pyridine (1 ml), cooled in an ice bath, was added methanesulfonyl chloride (0.31 ml). After 1 hour, ice was added and the white crystalline material was washed with water to give 3 (0.76 g, 83.5%).

EXAMPLE 2

L-Sorbose (30 g) was suspended in 2,2-dimethoxypropane (90 ml). 1,2-Dimethoxyethane (3 ml) containing tin(II) chloride (150 mg) was added. The mixture was refluxed, with stirring, for 2 hours until the solution was clear and then evaporated to a syrup. The syrup was dissolved in pyridine (60 ml) and cooled in an ice bath. Methanesulfonyl chloride (19.4 ml) was added. After storage in refrigerator for 16 hours and then at 25° C. for 4 hours, water (1000 ml) was added. The crystals produced were collected by filtration to give 3 (28.9 g, 51%). Recrystallization from ethanol gave 3 as colorless needles, m.p. 123°–124° C.

Anal. Calc. for $C_{13}H_{22}O_8S$: C, 46.14; H, 6.56; S, 9.48. Found: C, 46.25; H, 6.70, S, 9.11.

EXAMPLE 3

L-Sorbose (10 g) was suspended in 2,2-dimethoxypropane (30 ml). 1,2-Dimethoxyethane (1 ml) containing tin(II) chloride (30 mg) was added. The mixture was refluxed, with stirring, for 2.5 hours until the solution became clear. It was then evaporated to a syrup. The syrup was dissolved in pyridine (20 ml) and cooled in an ice bath. Methanesulfonyl chloride (6.45 ml) was added slowly. After storage at room temperature for 2.5 hours, water (400 ml) was added. Crystals produced were collected by filtration to give 3 (8.63 g, 46%).

EXAMPLE 4

L-Sorbose (4.122 g) was suspended in 2,2-dimethoxypropane (13.2 ml). Acetone (1 ml) containing tin(II) chloride (15 mg) was added. The mixture was refluxed, with stirring, for 100 minutes until the solution became clear. It was then evaporated to a syrup. The syrup, dissolved in pyridine, (8.2 ml) was cooled in an ice bath. Methanesulfonyl chloride (2.66 ml) was added slowly. After storage at room temperature for 2.5 hours, water (200 ml) was added. Produced crystals were collected by filtration to give 3 (3.08 g, 40%).

L-Fructose was prepared from compound 3 as shown in the following examples.

EXAMPLE 5

Compound 3 (2.5 g) was dissolved in acetone (20 ml) and 0.25% sulfuric acid in water (15 ml) was added. After storage at room temperature for 24 hours, the solution was made alkaline with a 9N sodium hydroxide solution (2 ml). The solution was then heated at 70°–80° C. for 48 hours, acidified with 18N sulfuric acid solution (1 ml), heated at 70°–80° C. for 20 minutes and then neutralized with 2N sodium hydroxide solution (5 ml). The mixture was taken to dryness and the residue extracted with ethanol (40 ml). The ethanol solution was concentrated to give L-fructose as a syrup (0.97 g, 73%). The syrup was contaminated with a small amount of by-products with lower mobility than L-fructose on silica gel thin layer chromatography. The mixture was purified on a silica gel column (4:1:0.7, v/v/v, ethyl acetatemethanol-water) to give a syrup product (0.83 g, 62%).

EXAMPLE 6

Compound 3 (3 g) dissolved in 60% acetic acid (30 ml) was heated at 40° C. for 3 hours. The mixture was made alkaline with 10N sodium hydroxide solution (40 ml), heated at 70° C. for 15 hours and then acidified with 18N sulfuric acid solution (30 ml). The salt was filtered off and the filtrate left at room temperature for 18 hours and 70° C. for 2 hours. The mixture was neutralized with 10N sodium hydroxide solution (3.5 ml). The salt was removed by ethanol precipitation. After filtration, the filtrate was concentrated, deionized with a column of Amberlite MG-1 ion-exchange resin, and eluted with water. The effluent was concentrated to give L-fructose as a syrup (1.21 g, 76%).

EXAMPLE 7

Compound 3 (1 g) is dissolved in acetone (10 ml) and 0.24% sulfuric acid in water (10 ml) is added. After storage at room temperature for 16 hours, the solution is neutralized with solid sodium hydrogencarbonate and filtered. Acetone is removed by evaporation until crystallization occurs to give 1,2-O-isopropylidene-3-O-mesyl-α-L-sorbofuranose. The crystalline material is dissolved in 5% potassium hydroxide (30 ml) and refluxed for 2.5 hours. The mixture is acidified to pH about 2 with 25% sulfuric acid in water. After storage at room temperature for 16 hours until the reaction is complete, the mixture is neutralized with 50% potassium hydroxide in water and taken to dryness. The residue is extracted with ethanol and the ethanol solution is concentrated to give L-fructose as a syrup. The syrup is deionized with a column of Amberlite MB-1 ion exchange resin.

The following examples illustrate the procedures for preparing L-fructose from L-sorbose by means of intermediate 10.

EXAMPLE 8

L-Sorbose (1, 40 g) was refluxed in 2,2-dimethoxypropane (100 ml) containing p-toluenesulfonic acid (500 mg) for 2 hours. The mixture was neutralized with a slight excess of methanolic sodium methoxide and concentrated to a syrup. The syrup was extracted with benzene (2×50 ml) and the benzene fraction was extracted with water (3×50 ml). The aqueous fraction saturated with sodium chloride was extracted with chloroform (3×100 ml). The chloroform was evaporated and the residue chromatographed on a silica gel column, eluted with 9:1 (v/v) hexane-acetone. Compound 9 was isolated as a crystalline material (1.6 g, 3.1%); $R_f$ (thin layer chromatography on silica gel in 9:1, v/v, chloroformacetone) 0.26. Recrystallization from ether gave 2, m.p. 109°–110° C.; lit. m.p. 108°–109° C.

Anal. Calc. for $C_{10}H_{18}O_6$: C, 51.27; H, 7.75. Found: C, 51.98; H, 7.99.

A solution of 9 (1.2 g) in pyridine (1.8 ml) was cooled in an ice bath and p-toluenesulfonyl chloride (3.3 g) in pyridine (5 ml) was added slowly. After storage at 25° C. for 2 days, ice was added and the mixture was extracted with chloroform (2×20 ml). The organic layer was washed twice with water, dried ($Na_2SO_4$) and evaporated to a syrup. Traces of pyridine in the residue were removed by co-evaporation with toluene to give 10 as a syrup (2.9 g, 100%), which was chromatographically pure; $R_f$ (thin layer chromatography on silica gel in 9:1, v/v, chloroform-acetone) 0.80; $[\alpha]_D^{25} +6°$ (c 2.5, chloroform). The mass spectrum showed the largest fragment ion at m/e 527 (M-CH3); P.m.r. (CDCl3); δ7.20–7.85 (m, 8H, $2C_6H_4CH_3$), 3.60–4.63 (m, 7H, H−1, −3, −4, −5, −6), 3.17 (s, 3H, OCH3), 2.43, 2.41 (s, s, 6H, $2C_6H_4\underline{C}H_3$) and 1.25, 1.15 (s, s, 6H, $2C(CH_3)_2$).

Anal. Calc. for $C_{24}H_{30}O_{10}S_2$: C, 53.13; H, 5.57; S, 11.82. Found: C, 53.21; H, 5.51; S, 11.74.

Compound 10 (2.3 g) was stirred in 60% acetic acid solution (23 ml) at 55° C. for 2.5 hours. The pH of the solution was raised to 5–6 with 10N sodium hydroxide solution and the mixture was extracted with chloroform (2×50 ml). The chloroform was evaporated to give 11 as a syrup (2 g, 94%); $R_f$ (thin layer chromatography on silica gel in 9:1, v/v, chloroform-acetone) 0.25; $[\alpha]_D^{25} -46°$ (c 1.8, chloroform). P.m.r. (CDCl3): δ7.06–7.85 (m, 8H, $2C_6H_4CH_3$), 3.40–4.80 (m, 7H, H−1, −3, −4, −5, −6), 3.20 (s, 3H, OCH3) and 2.40, 2.37 (s, s, 6H, $2C_6H_4\underline{C}H_3$).

Anal. Calc. for $C_{21}H_{26}O_{10}S_2$: C, 50.19; H, 5.22; S, 12.76. Found: C, 50.39; H, 5.48; S, 12.90.

To a solution of 11 (1.43 g) in methanol (1 ml) was added 2N sodium hydroxide solution (1 ml). After 2 hours at 40° C., 11 was converted to a single product, which showed positive in a vicinal epoxide test. Methanol (20 ml) was added and the solution was neutralized with 5N sulfuric acid solution. The salt was filtered and water (10 ml) was added. After evaporating the methanol, the aqueous solution was extracted with chloroform (2×50 ml). The chloroform was evaporated off to give 12 as a syrup (0.85 g, 90%); $[\alpha]_D^{25} -27°$ (c 2.5, chloroform). P.m.r. (CDCl$_3$); $\delta$7.10–7.87 (m, 4H, C$_6$H$_4$CH$_3$), 3.50–4.30 (m, 7H, H−1, −3, −4, −5, −6), 3.17 (s, 3H, OCH$_3$) and 2.40 (s, 3H, C$_6$H$_4$CH$_3$).

Anal. Calc. for C$_{14}$H$_{18}$O$_7$S: C, 50.90; H, 5.49; S, 9.17. Found: C, 50.76; H, 5.84; S, 9.47.

A solution of 12 (0.29 g) in a small amount of methanol was acidified with 1N sulfuric acid solution to pH 2–3. After storage at 25° C. for 2 days, 12 was cleanly converted to a single product. The mixture was neutralized with 1N sodium hydroxide solution and extracted with chloroform. The organic fraction was concentrated and the residue chromatographed on a silica gel column. Elution with 9:1 (v/v) chloroform-acetone gave 13 as a syrup (0.29 g, 95%). The mass spectrum showed the highest peak at m/e 317 (M—OCH$_3$). P.m.r. (CDCl$_3$): $\delta$7.10–7.83 (m,4H, C$_6$H$_4$CH$_3$), 3.40–4.30 (m,7H, H−1, −3, −4, −5, −6), 3.23 (s, 3H, OCH$_3$) and 2.43 (s, 3H, C$_6$H$_4$CH$_3$).

To a solution of 13 (7.5 g) in ethanol (50 ml) was added 10N sulfuric acid solution (125 ml). The mixture was heated at 70° C. for 1 hour and neutralized with 10N sodium hydroxide solution. After addition of ethanol and filtering off the salts the filtrate was concentrated. The residue was chromatographed on a silica gel column. Elution with 4:1:0.7 (v/v/v) ethyl acetate-methanol-water gave 7 as a syrup (3.6 g, 88%). The syrup was de-ionized with a column of Amberlite MB-1 ion-exchange resin and eluted with water. The effluent was concentrated to a syrup that crystallized from ethanol. Recrystallization from water-ethanol gave 7, m.p. 89°–90° C.; $[\alpha]_D^{25} +88°$ (water). P.m.r. (D$_2$O, 1% DSS): $\delta$3.37–4.13 (m).

Anal. Calc. for C$_6$H$_{12}$O$_6 \cdot \frac{1}{4}$H$_2$O: C, 39.02; H, 6.82. Found: C, 39.00; H, 6.87.

Compound 7 had the same mobility as D-fructose, but lower mobility than L-sorbose on silica gel thin layer chromatography (3:1:1, v/v/v, methyl ethyl ketone-methanol-acetic acid). The peracetylated derivatives of D-fructose and compound 7 also had the identical mobility on silica gel thin layer chromatography (9:1, v/v, chloroform-acetone).

EXAMPLE 9

A solution of 9 (18.7 g) in pyridine (25 ml) was cooled in an ice bath and p-toluenesulfonyl chloride (50.8 g) in pyridine (75 ml) was added slowly. After being kept at room temperature for 2 days, ice was added and the mixture was extracted with chloroform (300 ml×2). The organic layer was washed twice with water, dried (Na$_2$SO$_4$) and evaporated to a syrup (52.7 g, 100%), which was identified as 10.

Compound 10 (52.7 g) was stirred in 60% acetic acid (625 ml) at 55° C. for 2.5 hours. The solution was brought to pH of about 10 with 10N sodium hydroxide (625 ml) and heated at 40° C. for 3 hours. The reaction mixture was neutralized with 10N sulfuric acid (72 ml) and concentrated. The residue was triturated with ethanol (100 ml×3), filtered to removed much of the salt, and the ethanol solution was concentrated to a syrup. The residue was dissolved in ethanol (25 ml) and 10N sulfuric acid (100 ml) and heated at 80° C. for 30 minutes. The ethanol was evaporated off and the mixture was heated at 80° C. for 5 minutes. The reaction mixture was neutralized with 10N sodium hydroxide (100 ml) and the salt (Na$_2$SO$_4$) was removed by precipitation with ethanol. After filtration, the filtrate was concentrated to a syrup of L-fructose in a 52% yield from the starting material.

EXAMPLE 10

Compound 10 was stirred in 30% acetic acid at 55° C. for 5 hours. The solution was brought to pH of about 10 with 10N sodium hydroxide and heated at 40° C. for 3 hours. The reaction mixture was acidified with 10N sulfuric acid and heated at 80° C. with stirring for 30 minutes. The reaction mixture was neutralized with 10N sodium hydroxide and the salt was removed by repeated precipitation with ethanol. After filtration, the filtrate was concentrated to give L-fructose as a syrup in more than 85% yield.

Methanesulfonyl chloride may be used in place of p-toluenesulfonyl chloride as shown in example 11.

EXAMPLE 11

Methanesulfonyl chloride (1.5 g) was added to a solution of 9 (1.2 g) in pyridine (2 ml). After being kept at room temperature for 2 days, ice was added and the mixture was extracted with chloroform. The organic layer was washed with water and evaporated to give methyl 4,6-O-isopropylidene-1,3-di-O-methanesulfonyl-α-L-sorbofuranoside as a syrup. The syrup was stirred in 60% acetic acid at 55° C. for 2.5 hours. The solution was brought up to pH about 10 with 10N sodium hydroxide and heated at 40° C. for 3 hours. The reaction mixture was neutralized with 10N sulfuric acid and concentrated. The residue was triturated with ethanol. After the salt was filtered off, the ethanol solution was concentrated and the residue was dissolved in a mixture of ethanol and 10N sulfuric acid (1:4). The solution was heated to 80° C. for 30 min. Ethanol was evaporated off and the mixture was heated for 5 minutes. The reaction mixture was neutralized with 10N sodium hydroxide and the salt was removed by repeated precipitation with ethanol. After filtration, the filtrate was concentrated to give L-fructose in more than 85% yield.

What is claimed is:

1. A 3,4-anhydro-L-sorbose having the formula:

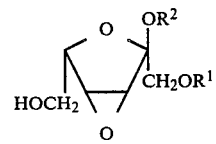

wherein R$^1$ represents a leaving group R$^2$ represents a (lower)alkyl group, or R$^1$ and R$^2$ taken together represent a blocking group.

2. The compound of claim 1, wherein said leaving group is selected from the group of mesyl and tosyl, and said blocking group is selected from the group of isopropylidene, benzylidene, ethylidene, sec. butylidene and cyclohexylidene.

3. A process for producing a product wherein the C3 and C4 atoms are in the L-fructo configuration from an L-sorbose derivative comprising L-sorbose having a hydroxyl group attached to the C4 atom, and an L group attached to the C3 atom, wherein L is a leaving group that will be eliminated upon subjection to alkaline conditions, comprising the steps of (A) subjecting the L-sorbose derivative to alkaline conditions, thereby forming a 3,4-oxirane ring wherein the 3,4-oxirane ring is arranged in a downward position in relation to Haworth projection, in which the ring oxygen atom is to the right and behind the plane of the paper; and (B) subjecting the product formed in Step (A) to a condition selected from the group consisting of heated strong alkaline, and at least mild acidic, thereby opening the 3,4-oxirane ring.

4. The process of claim 3, wherein the leaving group comprises mesyl or tosyl.

5. The process of claim 3, wherein Step (A) is carried out at room temperature.

6. The process of claim 3, wherein Step (B) ia carried out under heated strong alkaline conditions.

7. The process of claim 6, wherein said conditions include heating the product to a temperature of from 50° C. to boiling.

8. The process of claim 3, wherein Step (B) is carried out using at least mild acidic conditions.

9. The process of claim 3, wherein the L-sorbose derivative is produced from a starting material selected from the group consisting of L-sorbose, methyl L-sorbofuranoside, 1,2-O-isopropylidene-L-sorbofuranose, 1,2-O-isopropylidene-L-sorbopyranose, 2,3-O-isopropylidene-L-sorbofuranose, 2,3-O-isopropylidene-L-sorbopyranose, 1,3-O-isopropylidene-L-sorbofuranose, 1,3-O-isopropylidene-L-sorbopyranose, 1,2:4,6-di-O-isopropylidene-L-sorbofuranose, 2,3:4,6-di-O-isopropylidene-L-sorbofuranose, 1,3:4,5-di-O-isopropylidene-L-sorbofuranose, methyl 4,5-O-isopropylidene-L-sorbofuranoside, ethyl 4,6-O-isopropylidene-L-sorbofuranoside, methyl 1,3:4,6-di-O-isopropylidene-L-sorbofuranoside, and ethyl 1,3:4,6-di-O-isopropylidene-L-sorbofuranoside.

10. The process of claim 3, wherein the L-sorbose derivative is produced by a process wherein L-sorbose is reacted in the presence of a divalent catalyst to produce a compound having blocking groups in the 1,2 and 4,6 positions.

11. The process of claim 10, wherein the divalent catalyst is $SnCl_2$.

12. The process of claim 11, wherein the blocking groups are selected from the group consisting of isopropylidene, benzylidene, ethylidene, sec. butylidene and cyclohexylidene.

13. A process for producing L-fructose from L-sorbose comprising the steps of (A) reacting L-sorbose in the presence of a divalent catalyst to yield a product having blocking groups in the 1,2 and 4,6 positions, (B) reacting the product of Step (A) with methanesulfonyl chloride or toluenesulfonyl chloride, (C) reacting the product of Step (B) with acid to remove the 4,6 position blocking group, (D) reacting the product of Step (C) with a base, thereby forming a 3,4-oxirane ring, wherein the 3,4-oxirane ring is arranged in a downward position in relation to Haworth projection, in which the ring oxygen atom is to the right and behind the plane of the paper, (E) heating the product of Step (D) to from 50° to boiling, thereby opening the 3,4-oxirane ring, and (F) subjecting the product of Step (E) to acid hydrolysis to remove the 1,2 position blocking group, thereby yielding L-fructose.

14. The process of claim 13, wherein step (A) is carried out by reacting L-sorbose, in the presence of tin (II) chloride catalyst and a solvent, with a compound selected from the group consisting of 2,2-dimethoxypropane and acetone.

* * * * *